United States Patent
Kanda et al.

Patent Number: 4,898,941
Date of Patent: Feb. 6, 1990

[54] PROCESS FOR PREPARING DIPHENYLALKENE DERIVATIVES

[75] Inventors: Nobuo Kanda, Hirakata; Haruo Omura, Osaka; Yukihiro Abe, Nishinomiya; Mitsuru Kondo, Hyogo, all of Japan

[73] Assignee: Kanzaki Paper Manufacturing Co., Ltd., Tokyo, Japan

[21] Appl. No.: 83,815

[22] Filed: Aug. 11, 1987

[30] Foreign Application Priority Data

Aug. 22, 1986 [JP] Japan .................. 61-197622
Dec. 12, 1986 [JP] Japan .................. 61-297276

[51] Int. Cl.$^4$ ............ C07D 471/06; C07D 223/04; C07D 209/44; C07C 85/24
[52] U.S. Cl. .................... 540/596; 540/602; 540/609; 544/111; 544/165; 544/126; 544/128; 544/129; 544/142; 544/143; 546/98; 546/165; 546/190; 546/191; 546/246; 548/455; 548/482; 548/518; 548/491; 548/574; 548/577; 564/315; 564/330; 562/441; 549/473
[58] Field of Search .......... 546/98, 165, 186, 190, 546/246, 191; 544/111, 165, 126, 128, 129, 142, 143; 548/455, 569, 518, 574, 491, 577; 540/596, 602, 609; 564/315, 330; 549/473

[56] References Cited

U.S. PATENT DOCUMENTS

| | | | |
|---|---|---|---|
| 2,877,270 | 3/1959 | Benoze | 564/330 X |
| 3,530,198 | 9/1970 | Fenton | 568/835 X |
| 3,652,658 | 3/1972 | Fried et al. | 540/596 X |
| 3,677,752 | 7/1972 | Looker et al. | 564/315 X |
| 4,181,798 | 1/1980 | Morton, Jr. | 549/415 X |
| 4,319,066 | 3/1982 | Velenyi et al. | 570/201 X |

FOREIGN PATENT DOCUMENTS 0093143 5/1986 Japan .................. 564/330

OTHER PUBLICATIONS

Sheldon, et al(II), Organic Reactions, vol. 19, pp. 279–295, 300–313, 355, 370–374, 381–387, 420–421, (1972).

Jawdosiuk, et al., Chemical Abstracts, vol. 86: 72142w (1977).

Primary Examiner—Mukund J. Shah
Assistant Examiner—Diana G. Rivers
Attorney, Agent, or Firm—Armstrong, Nikaido, Marmelstein, Kubovcik & Murray

[57] ABSTRACT

A process for preparing a diphenylalkene derivative of the formula [II]

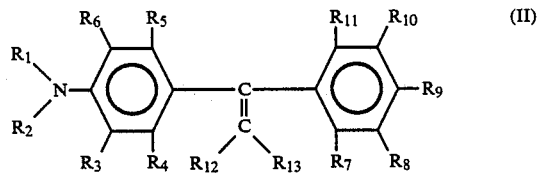

which comprises oxidizing a diphenylalkanoic acid derivative of the formula [I]

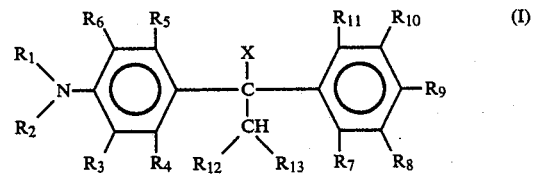

wherein $R_1$ and $R_2$ are each substituted or unsubstituted alkyl, substituted or unsubstituted alkenyl, substituted or unsubstituted alkynyl, substituted or unsubstituted cycloalkyl, substituted or unsubstituted aralkyl or substituted or unsubstituted aryl, $R_1$ and $R_2$ may form a heteroring together theirwith or with an adjacent benzene ring, $R_3$, $R_4$, $R_5$, $R_6$, $R_7$, $R_8$, $R_9$, $R_{10}$ and $R_{11}$ are each hydrogen atom, halogen atom, substituted or unsubstituted alkyl, substituted or unsubstituted hydroxyl or substituted or unsubstituted amino, $R_{12}$ and $R_{13}$ are each hydrogen atom or substituted or unsubstituted alkyl, X is carboxyl, amide, ester or halide thereof.

11 Claims, No Drawings

PROCESS FOR PREPARING DIPHENYLALKENE DERIVATIVES

The present invention relates to a novel process for preparing a diphenylalkene derivative which is useful as an intermediate of chromogenic material used for pressure-sensitive or heat-sensitive recording sheet.

Conventionally, as processes for producing bis(p,p'-substituted amino-1,1-diphenyl)ethylene derivative are known a method of employing 1,1-diphenylethyl carbinol derivative which is obtained from the reaction of benzophenone derivative and Grignard reagent, a method of using a Wittig reagent, a method of oxidizing 1,1-di-phenylethane derivative with lead peroxide, etc.

Among these processes, methods of using Grignard reagent or Wittig reagent require dehydration process and are not practised industrially. The third method is not also operable industrially, since the oxidation is conducted uneconomically at a low reactant concentration in a low conversion, which brings difficulty in separation of the starting material and the product.

An object of the invention is to provide a process for preparing a diphenylalkene derivative efficiently without the above conventional defects and with extremely simple purification and isolation operations.

Another object of the invention is to provide a novel diphenylalkanoic acid derivative which is useful as a starting material of the diphenylalkene derivative.

The above and other objects of the invention will become apparent from the following description.

The present invention provides a process for preparing a diphenylalkene derivative of the formula [II]

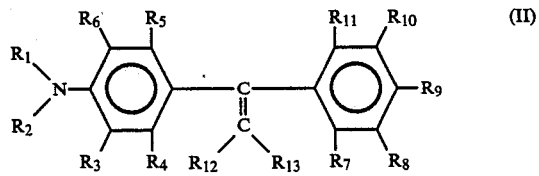

which comprises oxidizing a diphenylalkanoic acid derivative of the formula [I]

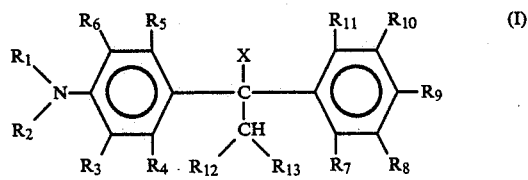

wherein $R_1$ and $R_2$ are each substituted or unsubstituted alkyl, substituted or unsubstituted alkenyl, substituted or unsubstituted alkynyl, substituted or unsubstituted cycloalkyl, substituted or unsubstituted aralkyl or substituted or unsubstituted aryl, $R_1$ and $R_2$ may form a heteroring together therewith or with an adjacent benzene ring, $R_3$, $R_4$, $R_5$, $R_6$, $R_7$, $R_8$, $R_9$, $R_{10}$ and $R_{11}$ are each hydrogen atom, halogen atom, substituted or unsubstituted alkyl, substituted or unsubstituted hydroxyl or substituted or unsubstituted amino, $R_{12}$ and $R_{13}$ are each hydrogen atom or substituted or unsubstituted alkyl, X is carboxyl, amide, ester or halide thereof.

The present invention also provides a novel diphenylalkanoic acid derivative of the formula [III]

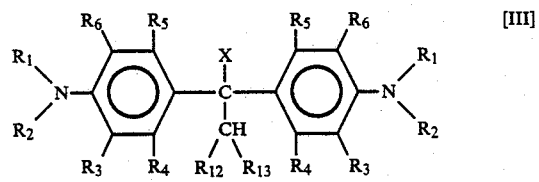

wherein $R_1$ to $R_6$, $R_{12}$, $R_{13}$ and X are same as above.

The reaction of the present invention can produce an expensive diphenylalkene derivative by oxidizing the diphenylalkanoic acid derivative of the formula [I] in a short period of time and without use of a specific apparatus. Further, in case the reaction is incomplete, the present process has an advantage that the diphenylalkanoic acid derivative can easily be removed or recovered by washing with an aqueous solution of sodium hydroxide.

Examples of oxidizing agents used in the above reaction are sodium persulfate, potassium persulfate, ammonium persulfate and like persulfates; sodium hypochlorite, sodium hypobromite and like halides; potassium permanganate, manganese dioxide and like manganese compounds; nitrous oxide, nitrogen monoxide, nitrogen dioxide and like nitrogen oxides; lead tetraacetate, lead-(II) oxide, lead(IV) oxide (lead dioxide) and like lead compounds; selenium dioxide; cobalt(III) salts; cerium-(IV) salts; ferric chloride; chloranil; etc. Further, it is possible to select and use an oxidizing agent which is described in "Oxidation and reduction of organic compounds" by Yoshiro Ogata published by Nankodo in 1963. These oxidizing agents can be used singly or in mixture of at least two of them. The amount of oxidizing agent used is suitably chosen depending on the kind thereof.

The reaction of the present invention can be conducted with or without use of a solvent.

As a solvent are used water, organic solvent which is inert in the reaction and a mixture of these solvents. Examples of useful solvents inert in the reaction are acetone, chloroform, tetrahydrofuran, dioxane, toluene, xylene, etc. The solvents are not limited particularly if they are inert in the reaction.

Although the reaction temperature is suitably determined depending on the kind of oxidizing agent, solvent, thermal stability of the formed diphenylalkene derivative, etc., it is preferable to conduct the oxidation generally at −5° C. to 150° C. to prevent side reactions.

Though some diphenylalkanoic acid derivatives do not form directly diphenylalkene derivatives but are converted into the corresponding carbinol derivative under the influence of water in the solvent, the carbinol derivative is easily dehydrated by heat, etc. during the recrystallization or like purification to form the corresponding diphenylalkene derivative. Generally, with above 50° C. in the reaction temperature, the diphenylalkene derivative can be obtained by a single step.

The diphenylalkanoic acid derivative of the formula [I] includes a derivative of the formula [III] having a symmetrical structure and a derivative of the formula [IV] or [V] having an asymmetrical structure.

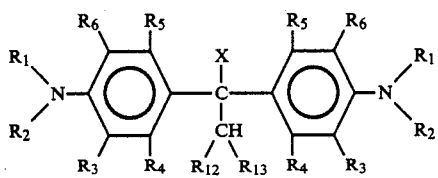

[III]

wherein $R_1$ to $R_6$, $R_{12}$, $R_{13}$ and X are same as above,

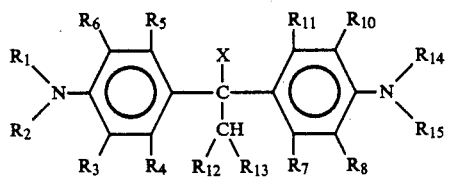

[IV]

wherein $R_{14}$ and $R_{15}$ are each hydrogen atom, substituted or unsubstituted alkyl, substituted or unsubstituted alkenyl, substituted or unsubstituted alkynyl, substituted or unsubstituted cycloalkyl, substituted or unsubstituted aralkyl or substituted or unsubstituted aryl, $R_{14}$ and $R_{15}$ may form a heteroring together therewith or with an adjacent benzene ring, $R_1$ and $R_{14}$ are not same group, $R_1$ to $R_8$, $R_{10}$ to $R_{13}$ and X are same as above,

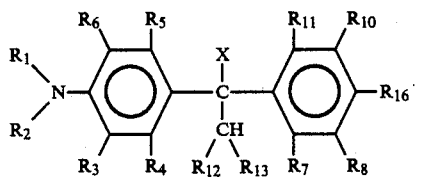

[V]

wherein $R_{16}$ is hydrogen atom, halogen atom, substituted or unsubstituted alkyl or substituted or unsubstituted hydroxyl, $R_1$ to $R_8$, $R_{10}$ to $R_{13}$ and X are same as above.

Among the above diphenylalkanoic acid derivatives of the formulae [I], [III], [IV] and [V], the compounds having the following definition of $R_1$ to $R_{16}$ and X are preferable, since the compounds can be obtained from inexpensive starting materials economically and afford diphenylalkene derivatives by oxidation reaction thereof which are easily isolated and purified.

$R_1$, $R_2$, $R_{14}$ and $R_{15}$ are each $C_{1\sim8}$ alkyl; $C_{2\sim4}$ alkyl substituted with $C_{1\sim4}$ alkoxyl; $C_{2\sim4}$ alkyl substituted with halogen atom; $C_{3\sim9}$ alkenyl; $C_{3\sim9}$ alkynyl; $C_{5\sim12}$ cycloalkyl; phenyl-$C_{1\sim4}$ alkyl unsubstituted or substituted with halogen atom, $C_{1\sim4}$ alkyl or $C_{1\sim4}$ alkoxyl; phenyl unsubstituted or substituted with halogen atom, $C_{1\sim4}$ alkyl or $C_{1\sim4}$ alkoxyl; or [$R_1$ and $R_2$] and [$R_{14}$ and $R_{15}$] each form a heteroring selected from among pyrrolidine ring, piperidine ring, morpholine ring, hexamethyleneimine ring, isoindoline ring, tetrahydroquinoline ring, indoline ring and julolidine ring, together therewith or with an adjacent benzene ring, $R_3$ to $R_{11}$ are each hydrogen atom; halogen atom; $C_{1\sim4}$ alkyl; $C_{1\sim4}$ alkoxyl; phenoxy unsubstituted or substituted with halogen atom, $C_{1\sim4}$ alkyl or $C_{1\sim4}$ alkoxyl; or substituted amino [—N($R_{17}$)($R_{18}$)], $R_{17}$ and $R_{18}$ are each hydrogen atom, $C_{1\sim8}$ alkyl; $C_{2\sim4}$ alkyl substituted with $C_{1\sim4}$ alkoxyl; $C_{2\sim4}$ alkyl substituted with halogen atom; $C_{3\sim9}$ alkenyl; $C_{3\sim9}$ alkynyl; $C_{5\sim12}$ cycloalkyl; $C_{1\sim4}$ acyl; phenyl-$C_{1\sim4}$ alkyl unsubstituted or substituted with halogen atom, $C_{1\sim4}$ alkyl or $C_{1\sim4}$ alkoxyl; or phenyl unsubstituted or substituted with halogen atom, $C_{1\sim4}$ alkyl or $C_{1\sim4}$ alkoxyl, $R_{17}$ and $R_{18}$ are not hydrogen atoms simultaneously, $R_{17}$ and $R_{18}$ may form a heteroring selected from among pyrrolidine ring, piperidine ring, morpholine ring, hexamethyleneimine ring, isoindoline ring, tetrahydroquinoline ring, indoline ring and julolidine ring, together therewith or with an adjacent benzene ring, $R_{12}$ and $R_{13}$ are each hydrogen atom or $C_{1\sim4}$ alkyl, $R_{16}$ is hydrogen atom; halogen atom; $C_{1\sim4}$ alkyl; $C_{1\sim4}$ alkoxyl; or phenoxy unsubstituted or substituted with halogen atom, $C_{1\sim4}$ alkyl or $C_{1\sim4}$ alkoxyl, X is carboxyl; $C_{1\sim8}$ alkyl ester thereof; phenyl-$C_{1\sim4}$ alkyl ester thereof, the phenyl group may be substituted with halogen atom, $C_{1\sim4}$ alkyl or $C_{1\sim4}$ alkoxyl; phenyl ester thereof, the phenyl group may be substituted with halogen atom, $C_{1\sim4}$ alkyl or $C_{1\sim4}$ alkoxyl; amide thereof; $C_{1\sim8}$ alkyl amide thereof; phenyl-$C_{1\sim4}$ alkyl amide thereof, the phenyl group may be substituted with halogen atom, $C_{1\sim4}$ alkyl or $C_{1\sim4}$ alkoxyl; anilide thereof which may be substituted with halogen atom, $C_{1\sim4}$ alkyl or $C_{1\sim4}$ alkoxyl; or chloride, bromide or iodide thereof.

The diphenylalkanoic acid derivative of the formula [III] having a symmetrical structure is easily prepared, for example, by condensing with dehydration a later-mentioned aniline derivative and a ketocarboxylic acid derivative in the presence of an acid catalyst. The derivative [IV] or [V] having an asymmetrical structure can be obtained, for example, by reacting 1-phenylpropionitrile derivative and p-halonitrobenzene in an aqueous alkaline solution, reducing the resulting 1-(p-nitrophenyl)-1-phenylpropionitrile derivative, hydrating the obtained 1-(p-aminophenyl)-1-phenylpropionitrile derivative and further alkylating the amino group to produce the corresponding 2,2-diphenylpropionic acid derivative.

Examples of diphenylalkanoic acid derivatives represented by the formula [I] are shown below.

2,2-Bis(4-dimethylaminophenyl)propionic acid, 2,2-bis(4-diethylaminophenyl)propionic acid, 2,2-bis{4-(N-methyl-N-ethyl)aminophenyl}propionic acid, 2,2-bis{4-(N-methyl-N-n-butyl)aminophenyl}propionic acid, 2,2-bis{4-(N-ethyl-N-n-butyl)aminophenyl}propionic acid, 2,2-bis{4-(N-ethyl-N-benzyl)aminophenyl}propionic acid, 2,2-bis{4-(N-ethyl-N-p-methylbenzyl)aminophenyl}propionic acid, 2,2-bis{4-(N-ethyl-N-p-methoxybenzyl)aminophenyl}propionic acid, 2,2-bis{4-(N-ethyl-N-p-chlorobenzyl)aminophenyl}propionic acid, 2,2-bis(4-dibenzylaminophenyl)propionic acid, 2,2-bis{4-di(p-chlorobenzyl)aminophenyl}propionic acid, 2,2-bis{4-(N-methyl-N-phenyl)aminophenyl}propionic acid, 2,2-bis{4-(N-methyl-N-p-tolyl)aminophenyl}propionic acid, 2,2-bis{4-(N-ethyl-N-p-tolyl)aminophenyl}propionic acid, 2,2-bis{4-(N-methyl-N-p-methoxyphenyl)aminophenyl}propionic acid, 2,2-bis{4-(N-methyl-N-p-chlorophenyl)aminophenyl}propionic acid, 2,2-bis{4-(N-methyl-N-cyclopentyl)aminophenyl}propionic acid, 2,2-bis{4-(N-methyl-N-cyclohexyl)aminophenyl}propionic acid, 2,2-bis{4-(N-ethyl-N-methoxyethyl)aminophenyl}propionic acid, 2,2-bis{4-(N-methyl-N-β-methoxyethyl)aminophenyl}propionic acid, 2,2-bis{4-(N-ethyl-N-ethoxyethyl)aminophenyl}propionic acid, 2,2-bis{4-(N-ethyl-N-phenoxyethyl)aminophenyl}propionic acid, 2,2-bis{4-(N-ethyl-N-chloroethyl)aminophenyl}propionic acid, 2,2-bis{4-(N-n-propyl-N-β-chloroethyl)aminophenyl}propionic acid, 2,2-bis{4-(N-ethyl-N-2,3-dimethoxypropyl)aminophenyl}propionic acid, 2,2-bis{4-(N-ethyl-N-tetrahydrofurfuryl)aminophenyl}propionic acid, 2,2-bis{4-(N-methyl-N-allyl)aminophenyl}propionic acid, 2,2-bis{4-(N-ethyl-N-allyl)aminophenyl}propionic acid, 2,2-bis{4-(N-isopropyl-N-allyl)aminophenyl}propionic acid, 2,2-bis{4-(N-methyl-N-propargyl)aminophenyl} propionic acid, 2,2-bis{4-(N-ethyl-N-propargyl)aminophenyl}propionic acid, 2,2-bis{4-N-ethyl-N-cinnamyl-)aminophenyl}propionic acid, 2,2-bis(4-diallylaminophenyl)propionic acid, 2,2-bis(4-dipropargylaminophenyl)propionic acid, 2,2-bis{4-(N-methyl-N-isopropyl)aminophenyl}propionic acid, 2,2-bis{4-(N-ethyl-N-isopropyl)aminophenyl}propionic acid, 2,2-bis{4-(N-ethyl-N-isobutyl)aminophenyl}propionic acid, 2,2-bis{4-(N-ethyl-N-isopentyl)aminophenyl}propionic acid, 2,2-bis{4-(N-ethyl-N-n-octyl)aminophenyl} propionic acid, 2,2-bis(2-methyl-4-dimethylaminophenyl)propionic acid, 2,2-bis(2-methyl-4-diethylaminophenyl)propionic acid, 2,2-bis(2-methoxy-4-dimethylaminophenyl)propionic acid, 2,2-bis(2-ethoxy-4-diethylaminophenyl)propionic acid, 2,2-bis(2-chloro-4-dimethylaminophenyl)propionic acid, 2,2-bis(2-chloro-4-diethylaminophenyl)propionic acid, 2,2-bis(2-acetylamino-4-dimethylaminophenyl)propionic acid, 2,2-bis(2-acetylamino-4-diethylaminophenyl)propionic acid, 2,2-bis(4-dimethoxyethylaminophenyl)propionic acid, 2,2-bis(4-diethoxyethylaminophenyl)propionic acid, 2,2-bis(4-pyrrolidinophenyl)propionic acid, 2,2-bis(4-2,5-dimethylpyrrolidinophenyl)propionic acid, 2,2-bis(4-piperidinophenyl)propionic acid, 2,2-bis(4-morpholinophenyl)propionic acid, 2,2-bis(4-hexamethyleneiminophenyl)propionic acid, 2,2-bis(4-isoindolinophenyl)propionic acid, 2,2-bis(1-methyl-1,2,3,4-tetrahydroquinoline-6-yl)propionic acid, 2,2-bis(1-ethyl-1,2,3,4-tetrahydroquinoline-6-yl)propionic acid, 2,2-bis(1,2,2,4-tetramethyl-1,2,3,4-tetrahydroquinoline-6-yl)propionic acid, 2,2-bis(1-methyl-indoline-5-yl)propionic acid, 2,2-bis(1-ethyl-indoline-5-yl)propionic acid, 2,2-bis(julolidine-9-yl)propionic acid, 2,2-bis(4-dimethylaminophenyl)butyric acid, 2,2-bis(4-diethylaminophenyl)butyric acid, 2,2-bis(4-morpholinophenyl)butyric acid, 2,2-bis(4-pyrrolidinophenyl)butyric acid, 2,2-bis(4-dimethylaminophenyl)valeric acid, 2,2-bis(4-diethylaminophenyl)valeric acid, 2,2-bis(4-morpholinophenyl)valeric acid, 2,2-bis(4-pyrrolidinophenyl)valeric acid, 2,2-bis(4-diethylaminophenyl)caproic acid, and like diphenylalkanoic acids having a symmetrical structure;

2-(4-pyrrolidinophenyl)-2-(4-dimethylaminophenyl)propionic acid, 2-(4-pyrrolidinophenyl)-2-(4-diethylaminophenyl)propionic acid, 2-(4-piperidinophenyl)-2-(4-dimethylaminophenyl)propionic acid, 2-(4-morpholinophenyl)-2-(4-dimethylaminophenyl)propionic acid, 2-(4-hexamethyleneiminophenyl)-2-(4-dimethylaminophenyl)propionic acid, 2-(4-pyrrolidinophenyl)-2-(4-N-ethyl-N-benzylaminophenyl)propionic acid, 2-(4-piperidinophenyl)-2-(4-N-ethyl-N-benzylaminophenyl)propionic acid, 2-(4-morpholinophenyl)-2-(4-N-ethyl-N-benzylaminophenyl)propionic acid, 2-(4-hexamethyleneiminophenyl)-2-(4-N-ethyl-N-benzylaminophenyl)propionic acid, 2-(4-pyrrolidinophenyl)-2-(4-N-methyl-N-p-tolylaminophenyl)propionic acid, 2-(4-piperidinophenyl)-2-(4-N-methyl-N-p-tolylaminophenyl)propionic acid, 2-(4-morpholinophenyl)-2-(4-N-methyl-N-p-tolylaminophenyl)propionic acid, 2-(4-hexamethyleneiminophenyl)-2-(4-N-methyl-N-p-tolylaminophenyl)propionic acid, 2-(4-pyrrolidinophenyl)-2-(2-methyl-4-diethylaminophenyl)propionic acid, 2-(4-pyrrolidinophenyl)-2-(2-methoxy-4-diethylaminophenyl)propionic acid, 2-(4-pyrrolidinophenyl)-2-(3-methyl-4-diethylaminophenyl)propionic acid, 2-(4-pyrrolidinophenyl)-2-(3-ethoxy-4-diethylaminophenyl)propionic acid, 2-(4-dimethylaminophenyl)-2-(2-methyl-4-pyrrolidinophenyl)propionic acid, 2-(4-dimethylaminophenyl)-2-(2-methyl-4-dimethylaminophenyl)propionic acid, 2-(4-dimethylaminophenyl)-2-(2-methyl-4-dimethylaminophenyl)propionic acid, 2-(3-dimethylaminophenyl)-2-(4-dimethylaminophenyl)propionic acid, 2-(4-acetylaminophenyl)-2-(4-dimethylaminophenyl)propionic acid, 2-phenyl-2-(4-dimethylaminophenyl)propionic acid, 2-phenyl-2-{4-(N-ethyl-N-allyl)aminophenyl}propionic acid, 2-phenyl-2-(4-pyrrolidinophenyl)propionic acid, 2-(4-methylphenyl)-2-(4-pyrrolidinophenyl)propionic acid, 2-(4-ethylphenyl)-2-(4-pyrrollidinophenyl)propionic acid, 2-(4-chlorophenyl)-2-(4-pyrroliodinophenyl)propionic acid, 2-(4-methoxyphenyl)-2-(4-dimethylaminophenyl)propionic acid, 2-(4-ethoxyphenyl)-2-(4-dimethylaminophenyl)propionic acid, 2-(2,4-dimethoxyphenyl)-2-(4-diethylaminophenyl)propionic acid, 2-(4-methylphenyl)-2-(4-di-n-butylaminophenyl)propionic acid, 2-(4-methoxyphenyl)-2-(4-pyrrolidinophenyl)propionic acid, 2-(4-ethoxyphenyl)-2-(4-pyrrolidinophenyl)propionic acid, 2-(4-phenoxyphenyl)-2-(4-pyrrolidinophenyl)propionic acid, 2-(4-ethoxyphenyl)-2-(4-diethylaminophenyl)propionic acid, 2-(4-butoxyphenyl)-2-(4-pyrrolidinophenyl)propionic acid, 2-(2-methyl-4-methoxyphenyl)-2-(4-dimethylaminophenyl)propionic acid, 2-(2-methyl-4-methoxyphenyl)-2-(4-pyrrolidinophenyl)propionic acid, 2-(4-methoxyphenyl)-2-(2-methyl-4-pyrrolidinophenyl)propionic acid, 2-(4-ethoxyphenyl)-2-(3-ethoxy-4-diethylaminophenyl)propionic acid, 2-(3-methylphenyl)-2-{4-(N-methyl-N-benzyl)aminophenyl}propionic acid, 2-(3,5-dichlorophenyl)-2-(4-hexamethyleneiminophenyl)propionic acid, 2-(3-ethylphenyl)-2-(4-morpholinophenyl)propionic acid, 2-phenyl-2-(4-dibenzylaminophenyl)propionic acid, 2-(2,3-dimethylphenyl)-2-{4-(N-ethyl-N-phenyl)aminophenyl}propionic acid, 2-phenyl-2-(1-methyl-1,2,3,4-tetrahydroquinoline-6-yl)propionic acid, 2-(4-methoxyphenyl)-2-(1-ethyl-1,2,3,4-tetrahydroquinoline-6-yl)propionic acid, 2-phenyl-2-(1-n-propyl-1,2,3,4-tetrahydroquinoline-6-yl)propionic acid, 2-(4-methoxyphenyl)-2-(4-dimethylaminophenyl)-butyric acid, 2-(4-methoxyphenyl)-2-(4-pyrrolidinophenyl)butyric acid, 2-(4-ethoxyphenyl)-2-(4-pyrrolidinophenyl)butyric acid, 2-(4-methoxyphenyl)-2-(1-ethyl-1,2,3,4-tetrahydroquinoline-6-yl)butyric acid, 2-(4-ethoxyphenyl)-2-(4-diethylaminophenyl)butyric acid, 2-(4-butoxyphenyl)-2-(4-piperidinophenyl)butyric acid, 2-(2-methyl-4-methoxyphenyl)-2-(4-diethylaminophenyl)butyric acid, 2-(4-ethoxyphenyl)-2-(3-ethoxy-4-diethylaminophenyl)butyric acid and like diphenylalkanoic acids having an asymmetrical structure;

methyl ester, ethyl ester, propyl ester, butyl ester, benzyl ester, methylbenzyl ester, methoxybenzyl ester, chlorobenzyl ester, phenyl ester, tolyl ester, methoxyphenyl ester, chlorophenyl ester and like esters of the diphenylalkanoic acids;

amide, methylamide, ethylamide, propylamide, butylamide, dimethylamide, diethylamide, dipropylamide, dibutylamide, benzylamide, N-methyl-benzylamide, N-ethyl-p-methyl-benzylamide, anilide, N-methyl-anilide, toluidide, N-methyl-p-toluidide, and like amides of the diphenylalkanoic acids;

chloride, bromide, iodide and like halides of the diphenylalkanoic acids, etc.

Among the above diphenylalkanoic acid derivatives of the formulae [III], [IV] and [V], the following derivatives of the formulae [III'], [IV'] and [V'] are preferable since the desired diphenylalkene derivatives are obtained in a high yield from these derivatives, and further the derivatives of the formulae [III''], [IV''] and [V''] are more preferable which are inexpensively available.

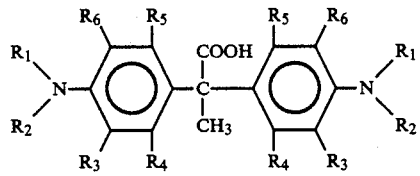

[III']

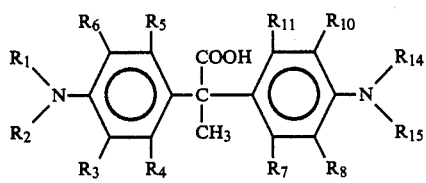

[IV']

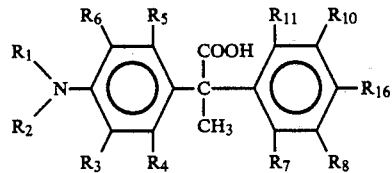

[V']

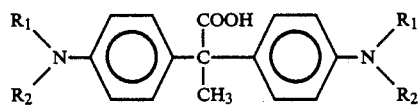

[III'']

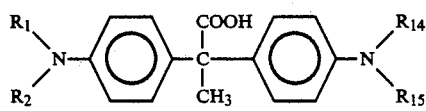

[IV'']

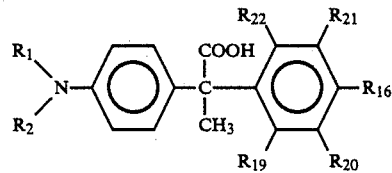

[V'']

wherein $R_1$ to $R_8$, $R_{10}$, $R_{11}$, $R_{14}$ to $R_{16}$ are same as above, $R_{19}$ to $R_{22}$ are each same as $R_{16}$.

Conventionally, as a process for producing the above 4,4'-diaminodiphenylalkanoic acid derivatives having a symmetrical structure is known solely a method of preparing 2,2-bis(4-aminophenyl)propionic acid methyl ester by reacting 2,2-diphenylpropionic acid methyl ester with nitric acid and reducing with Raney nickel the nitrated product.

However, this method is likely to involve side reactions and low in yield. Further, the method is carried out only by a limited apparatus because of using Raney nickel. Accordingly, this method is not necessarily advantageous process industrially.

The inventors of the present invention have found that the 4,4'-diaminodiphenylalkanoic acid derivative having a symmetrical structure can be prepared by the following method without the above conventional defects and with an excellent reaction efficiency and simple purification and isolation operations.

A process for preparing a diphenylalkanoic acid derivative of the formula [III]

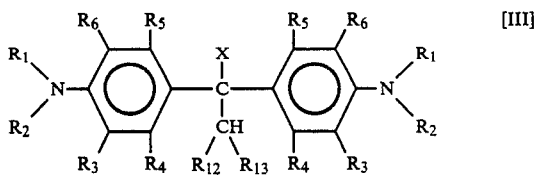

[III]

which comprises reacting an aniline derivative of the formula [VI] with a ketocarboxylic acid derivative of the formula [VII]

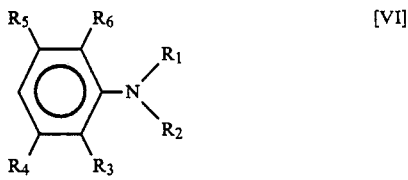

[VI]

[VII]

wherein $R_1$ and $R_2$ are each substituted or unsubstituted alkyl, substituted or unsubstituted alkenyl, substituted or unsubstituted alkynyl, substituted or unsubstituted cycloalkyl, substituted or unsubstituted aralkyl or substituted or unsubstituted aryl, $R_1$ and $R_2$ may form a heteroring together theirwith or with an adjacent benzene ring, $R_3$, $R_4$, $R_5$ and $R_6$ are each hydrogen atom, halogen atom, substituted or unsubstituted alkyl, substituted or unsubstituted hydroxyl or substituted or unsubstituted amino, $R_{12}$ and $R_{13}$ are each hydrogen atom or substituted or unsubstituted alkyl, X is carboxyl, amide, ester or halide thereof.

The diphenylalkanoic acid derivative of the formula [III] can be obtained by condensing with dehydration the aniline derivative of the formula [VI] and the ketocarboxylic acid derivative of the formula [VII] at a temperature from room temperature to 200° C. for several to several tens hours.

The above condensation reaction can be conducted with or without use of a solvent. When a solvent is not used, the process has an advantage to become simple because the solvent needs not be removed.

As a solvent are used water, organic solvent which is inert in the reaction and a mixture of these solvents. Examples of useful solvents inert in the reaction are acetone, chloroform, tetrahydrofuran, dioxane, toluene, xylene, etc. The solvents are not limited particularly if they are inert in the reaction.

Although the reaction can be conducted without use of a dehydrating(condensing) agent, the reaction temperature is lowered by the use thereof. The dehydrating agent includes hydrochloric acid, sulfuric acid, polyphosphoric acid, pyrophosphoric acid, phosphoric acid and like inorganic acids; p-toluenesulfonic acid, formic acid, acetic acid, propionic acid and like organic acids; tin chloride, zinc chloride, aluminum chloride, iron chloride and like anhydrous metal chlorides; phosphorus trichloride, phosphorus pentachloride, phosphorus pentoxide, etc. Among the above, preferably used are hydrochloric acid, sulfuric acid, phosphoric acid, formic acid, acetic acid and propionic acid which are also usable as a solvent. The amount of the dehydrating agent is suitably adjusted depending on the kind thereof.

Examples of useful compounds of the formula [VI] are N,N-dimethylaniline, N,N-diethylaniline, N,N-dipropylaniline, N,N-dibutylaniline, N,N-dimethyl-m-toluidine, N,N-diethyl-m-toluidine, N,N-dimethyl-m-chloroaniline, N,N-diethyl-m-chloroaniline, N,N-dimethyl-m-anisidine, N,N-diethyl-m-phenetidine, N-methyl-N-isopropylaniline, N-methyl-N-n-butylaniline, N-methyl-N-benzylaniline, N-ethyl-N-p-chlorobenzylaniline, N,N-diphenylaniline, N,N-dipropargylaniline, N-methyl-N-ethoxyethylaniline, N-ethyl-N-ethoxyethylaniline, N-methyl-N-2,3-dimethoxypropylaniline, N-ethyl-N-2,3-dimethoxypropylaniline, N-ethyl-N-$\beta$-phenoxyethyaniline, N-ethyl-N-$\beta$-chloroethylaniline, N-n-propyl-N-$\beta$-chloroethylaniline, N-ethyl-N-$\beta$-chloroethyl-m-toluidine, N-ethyl-N-$\beta$-cyanoethylaniline, N-ethyl-N-$\beta$-cyanoethyl-m-toluidine, N-methyldiphenylamine, 4-methoxy-N-methyldiphenylamine, N-phenylpyrrolidine, N-phenylmorpholine, N-phenylpiperidine, N-phenylhexamethyleneimine, N-3-methylphenylpiperidine, N-3-methylphenylmorpholine, 1-phenyl-2,5-dimethylpyrrolidine, N-methylindoline, N-phenylisoindoline, N-benzyl-N-ethylaniline, N,N-dibenzylaniline, N-p-chlorobenzyl-N-allylaniline, N-methyl-N-allylaniline, N-allyl-N-phenylaniline, N-$\beta$-chloroethyl-N-ethyl-2,3-dimethylaniline, N-$\beta$-chloroethyl-N-benzyl-2-methyl-3-chloroaniline, N-ethoxyethyl-N-ethyl-m-toluidine, N-2-dimethylaminoethyl-N-methylaniline, N-methyl-N-cyclohexylaniline, N-cyclohexyl-N-ethyl-o-toluidine, N,N-dimethyl-3,5-dimethoxyaniline, N-3-methylphenylpyrrolidine, N-3-acetylaminophenylpyrrolidine, N-2-chlorophenylpyrrolidine, N-3-methyl-5-chlorophenylpyrrolidine, N,N-dimethyl-3-acetylaminoaniline, N-m-methoxybenzyl-N-propargylaniline, N-p-methylbenzyl-N-isopropylaniline, julolidine, 1-methyl-1,2,3,4-tetrahydroquinoline, 1,2,2,4-tetramethyl-1,2,3,4-tetrahydroquinoline, N-ethyl-N-tetrahydrofurfurylaniline, N-$\alpha$-naphthyl-N-methylaniline, N-ethyl-N-isopropyl-o-bromoaniline, N-p-methylphenyl-N-ethylaniline, N-p-methylphenyl-N-butylaniline, etc.

Examples of useful ketocarboxylic acid derivatives of the formula [VII] are carboxylic acids such as pyruvic acid, 2-ketobutyric acid, 2-ketovaleric acid, 2-ketocaproic acid, ketoenanthic acid, ketocaprylic acid, ketocapric acid and ketoundecanoic acid; ester derivatives such as methyl ester, ethyl ester, propyl ester, butyl ester, benzyl ester, methylbenzyl ester, methoxybenzyl ester, chlorobenzyl ester, phenyl ester, tolyl ester, methoxyphenyl ester, chlorophenyl ester and cyclohexyl ester of the ketocarboxylic acid; amide derivatives such as amide, methylamide, ethylamide, propylamide, butylamide, dimethylamide, diethylamide, dipropylamide, dibutylamide, ethylbutylamide, benzylamide, N-methyl-benzylamide, anilide, N-methyl-anilide, toluidide, N-ethyl-toluidide, p-ethoxyanilide and p-chloroanilide of the ketocarboxylic acid; halogen derivatives such as chloride, bromide and iodide of the ketocarboxylic acid.

The ketocarboxylic acid derivative of the formula [VII] is usually used in an amount of about 0.3 to 3 moles, more preferably about 0.5 to 1.5 moles per mole of the aniline derivative of the formula [VI]. After the completion of reaction, the diphenylalkanoic acid derivative can be isolated by a usual method such as distillation, crystallization, extraction, etc.

The above diphenylalkanoic acid derivatives having a symmetrical structure of the formula [III] are novel compounds and are useful as a starting material of 4,4'-diaminodiphenylethylene derivative, this derivative being an intermediate of chromogenic material used for pressure-sensitive or heat-sensitive recording sheet. Further, the derivative [III] is useful as an organic photosemiconductor used for electrophotocopying.

Examples of diphenylalkene derivatives of the formula [II] are given below.

1,1-Bis(4-dimethylaminophenyl)ethylene, 1,1-bis(4-diethylaminophenyl)ethylene, 1,1-bis{4-(N-ethyl-N-allyl)aminophenyl}ethylene, 1,1-bis{4-(N-ethyl-N-propargyl)aminophenyl}ethylene, 1,1-bis{4-di(p-chlorobenzyl)aminophenyl}ethylene, 1,1-bis(4-dimethylaminophenyl)1-propene, 1,1-bis(4-diethylaminophenyl)-1-propene, 1,1-bis(4-dimethylamino-2-methylphenyl)ethylene, 1,1-bis(4-diethylamino-2-methylphenyl)ethylene, 1,1-bis(4-dimethylamino-2-methoxyphenyl)ethylene, 1,1-bis(4-diethylamino-2-methoxyphenyl)ethylene, 1,1-bis{4-(N-methyl-N-ethyl)aminophenyl}ethylene, 1,1-bis{4-(N-methyl-N-n-butyl)aminophenyl}ethylene, 1,1-bis{4-(N-methyl-N-cyclohexyl)aminophenyl}ethylene, 1,1-bis{4-(N-ethyl-N-$\beta$-chloroethyl)aminophenyl}ethylene, 1,1-bis{4-(N-methyl-N-$\beta$-methoxyethyl)aminophenyl}ethylene, 1,1-bis{4-(N-methyl-N-benzyl)aminophenyl}ethylene, 1,1-bis{4-(N-ethyl-N-benzyl)aminophenyl}ethylene, 1,1-bis{4-(N-ethyl-N-p-chlorobenzyl)aminophenyl}ethylene, 1,1-bis{4-(N-methyl-N-phenyl)aminophenyl}ethylene, 1,1-bis{4-(N-methyl-N-p-tolyl)aminophenyl}ethylene, 1,1-bis{4-(N-methyl-N-p-methoxyphenyl)aminophenyl}ethylene, 1,1-bis{4-(N-ethyl-N-p-methoxyphenyl)aminophenyl}ethylene, 1,1-bis(4-dimethylamino-2-methylphenyl)-1-propene, 1,1-bis(4-diethylamino-2-methylphenyl)-1-propene, 1,1-bis(4-dimethylamino-2-methoxyphenyl)-1-propene, 1,1-bis(4-diethylamino-2-methoxyphenyl)-1-propene, 1,1-bis(4-pyrrolidinophenyl)ethylene, 1,1-bis(4-piperidinophenyl)ethylene, 1,1-bis(4-morpholinophenyl)ethylene, 1,1-bis(4-hexamethyleneiminophenyl)ethylene, 1,1-bis(2-methyl-4-pyrrolidinophenyl)-ethylene, 1,1-bis(2-methyl-4-piperidinophenyl)ethylene, 1,1-bis(2-methyl-4-morpholinophenyl)ethylene, 1,1-bis(2-methyl-4-hexamethyleneiminophenyl)ethylene, 1,1-bis(2-methoxy-4-pyrrolidinophenyl)ethylene, 1,1-bis(2-methoxy-4-piperidinophenyl)ethylene, 1,1-bis(2-methoxy-4-morpholinophenyl)ethylene, 1,1-bis-(2-methoxy-4-hexamethyleneiminophenyl)ethylene, 1-(4-pyrrolidinophenyl)-1-(4-dimethylaminophenyl)ethylene, 1-(4-pyrrolidinophenyl)-1-(4-diethylaminophenyl)ethylene, 1-(4-piperidinophenyl)-1-(4-dimethylaminophenyl)ethylene, 1-(4-morpholinophenyl)-1-(4-dimethylaminophenyl)ethylene, 1-(4-hexamethyleneiminophenyl)-1-(4-dimethylaminophenyl)ethylene, 1-(4-pyrrolidinophenyl)-1-(4-N-ethyl-N-benzylaminophenyl)ethylene, 1-(4-piperidinophenyl)-1-(4-N-ethyl-N-benzylaminophenyl)ethylene, 1-(4-morpholinophenyl)-1-(4-N-ethyl-N-benzylaminophenyl)ethylene, 1-(4-hexamethyleneiminophenyl)-1-(4-N-ethyl-N-benzylaminophenyl)ethylene, 1-(4-pyrrolidinophenyl)-1-(4-N-methyl-N-p-tolylaminophenyl)ethylene, 1-(4-piperidinophenyl)-1-(4-N-methyl-N-p-tolylaminophenyl)ethylene, 1-(4-morpholinophenyl)-1-(4-N-methyl-N-p-tolylaminophenyl)ethylene, 1-(4-hexamethyleneiminophenyl)-1-(4-N-methyl-N-p-tolylaminophenyl)ethylene, 1-(4-pyrrolidinophenyl)-1-(2-methyl-4-diethylaminophenyl)ethylene, 1-(4-pyrrolidinophenyl)-1-(2-methoxy-4-diethylaminophenyl)ethylene, 1,1-bis(4-pyrrolidinophenyl)-1-propene, 1,1-bis(4-piperidinophenyl)-1-propene, 1,1-bis(4-morpholinophenyl)-1-propene, 1,1-bis(4-hexamethyleneiminophenyl)-1-propene, 1,1-bis(julolidine-9-yl)ethylene, 1,1-bis(1-methyl-1,2,3,4-tetrahydroquinoline-6-yl)ethylene, 1,1-bis(1-ethyl-1,2,3,4-tetrahydroquinoline-6-yl)ethylene, 1,1-bis(4-dimethylamino-3-methylphenyl)ethylene, 1,1-bis(4-diethylamino-2,3-dimethylphenyl)ethylene, 1,1-bis(4-dimethylamino-3-methoxyphenyl)ethylene, 1,1-bis(4-diethylamino-3,6-dimethoxyphenyl)ethylene, 1,1-bis(4-dimethylamino-3-chlorophenyl)-1-propene, 1,1-bis(4-diethylamino-3-methylphenyl)-1-propene, 1,1-bis(4-dimethylamino-2,3-dimethoxyphenyl)-1-propene, 1,1-bis(4-diethylamino-3-methoxyphenyl)-1-propene, 1,1-bis(4-pyrrolidino-3-methylphenyl)ethylene, 1,1-bis(4-morpholino-3-ethylphenyl)ethylene, 1,1-bis(2-chloro-4-hexamethyleneiminophenyl)ethylene, 1,1-bis(4-pyrrolidino-3-propoxyphenyl)ethylene, 1,1-bis(4-piperidino-3-methoxyphenyl)ethylene, 1,1-bis(4-morpholino-2,3-dichlorophenyl)ethylene, 1,1-bis(3-methoxy-4-hexamethyleneiminophenyl)ethylene, 1-(4-pyrrolidinophenyl)-1-(3-methyl-4-diethylaminophenyl)ethylene, 1-(4-pyrrolidinophenyl)-1-(3-ethoxy-4-diethylaminophenyl)ethylene, 1-(4-dimethylaminophenyl)-1-(2-methyl-4-pyrrolidinophenyl)ethylene, 1-(4-dimethylaminophenyl)-1-(2-methyl-4-dimethylaminophenyl)ethylene, 1-(4-diethylaminophenyl)-1-(2-methyl-4-dimethylaminophenyl)ethylene, 1-(3-dimethylaminophenyl)-1-(4-dimethylaminophenyl)ethylene, 1-(4-acetylaminophenyl)-1-(4-dimethylaminophenyl)ethylene, 1-phenyl-1-(4-dimethylaminophenyl)ethylene, 1-phenyl-1-{4-(N-ethyl-N-allyl)aminiophenyl}ethylene, 1-phenyl-1-(4-pyrrolidinophenyl)ethylene, 1-(4-methylphenyl)-1-(4-pyrrolidinophenyl)ethylene, 1-(4-ethylphenyl)-1-(4-pyrrolidinophenyl)ethylene, 1-(4-chlorophenyl)-1-(4-pyrrolidinophenyl)ethylene, 1-(4-methoxyphenyl)-1-(4-dimethylaminophenyl)ethylene, 1-(4-ethoxyphenyl)-1-(4-dimethylaminophenyl)ethylene, 1-(2,4-dimethoxyphenyl)-1-(4-diethylaminophenyl)ethylene, 1-(4-methylphenyl)-1-(4-di-n-butylaminophenyl)ethylene, 1-(4-methoxyphenyl)-1-(4-pyrrolidinophenyl)ethylene, 1-(4-ethoxyphenyl)-1-(4-pyrrolidinophenyl)ethylene, 1-(4-phenoxyphenyl)-1-(4-pyrrolidinophenyl)ethylene, 1-(4-ethoxyphenyl)-1-(4-diethylaminophenyl)ethylene, 1-(4-butoxyphenyl)-1-(4-piperidinophenyl)ethylene, 1-(2-methyl-4-methoxyphenyl)-1-(4-dimethylaminophenyl)ethylene, 1-(2-methyl-4-methoxyphenyl)-1-(4-pyrrolidinophenyl)ethylene, 1-(4-methoxyphenyl)-1-(2-methyl-4-pyrrolidinophenyl)ethylene, 1-(4-ethoxyphenyl)-1-(3-ethoxy-4-diethylaminophenyl)ethylene, 1-(3-methylphenyl)-1-{4-(N-methyl-N-benzyl)aminophenyl}ethylene, 1-(3,5-dichlorophenyl)-1-(4-hexamethyleneiminophenyl)ethylene, 1-(3-ethylphenyl)-1-(4-morpholinophenyl)ethylene, 1-phenyl-1-(4-dibenzylaminophenyl)ethylene, 1-(2,3-dimethylphenyl)-1-{4-(N-ethyl-N-phenyl)aminophenyl}ethylene, 1-(4-methoxyphenyl)-1-(4-dimethylaminophenyl)-1-propene, 1-(4-methoxyphenyl)-1-(4-pyrrolidinophenyl)-1-propene, 1-(4-ethoxyphenyl)-1-(4-pyrrolidinophenyl)-1-propene, 1-(4-methoxyphenyl)-1-(1-ethyl-1,2,3,4-tetrahydroquinoline-6-yl)-1-propene, 1-(4-ethoxyphenyl)-1-(4-diethylaminophenyl)-1-propene, 1-(4-butoxyphenyl)-1-(4-piperidinophenyl)-1-propene, 1-(2-methyl-4-methoxyphenyl)-1-(4-diethylaminophenyl)-1-propene, 1-(4-ethoxyphenyl)-1-(3-ethoxy-4-diethylaminophenyl)-1-propene, 1-phenyl-1-(1-methyl-1,2,3,4-tetrahydroquinoline-6-yl)ethylene, 1-(4-methoxyphenyl)-1-(1-ethyl-1,2,3,4-tetrahydroquinoline-6-yl)ethylene, 1-phenyl-1-(1-n-propyl-1,2,3,4-tetrahydroquinoline-6-yl)ethylene, etc.

The invention will be described below in more detail with reference to examples without limiting the scope thereof, in which percentages are all by weight.

EXAMPLE 1

Synthesis of 2,2-bis(4-dimethylaminophenyl)propionic acid

Into 40 ml of 20% aqueous solution of sulfuric acid was dissolved 20 g of N,N-dimethylaniline. To the solution were added 8.4 g of pyruvic acid and 0.2 g of p-toluenesulfonic acid and the mixture was heated with reflux for 24 hours. The reaction mixture was, after cooled, diluted with 200 ml of water and adjusted to pH 6 with addition of 20% aqueous solution of sodium hydroxide. The precipitated crystal was collected by filtration which was 18.0 g (yield 70%) of 2,2-bis(4-dimethylaminophenyl)propionic acid, having a melting point of 152°~154° C.

EXAMPLE 2

Synthesis of 2,2-bis(4-pyrrolidinophenyl)propionic acid

Into 40 ml of 20% aqueous solution of sulfuric acid was dissolved 20 g of N-phenylpyrrolidine. To the solution was added 7.2 g of pyruvic acid and the mixture was heated with reflux for 16 hours. The reaction mixture was, after cooled, diluted with 300 ml of water and adjusted to pH 6 with addition of 20% aqueous solution of sodium hydroxide. The precipitated crystal was collected by filtration. The crystal was recrystallized from benzene to obtain 18.5 g (yielded 75%) of 2,2-bis(4-pyrrolidinophenyl)propionic acid as white crystal, having a melting point of 174°~176° C.

EXAMPLE 3

Synthesis of 2,2-bis(4-morpholinophenyl)propionic acid

Into 12 ml of 6N—HCl solution was dissolved 4.65 g of N-phenylmorpholine. To the solution was added 1.5 g of pyruvic acid and the mixture was heated with reflux for 20 hours. The reaction mixture was, after cooled, diluted with 100 ml of water and adjusted to pH 6 with addition of 20% aqueous solution of sodium hydroxide. The precipitated crystal was collected by filtration which was 3.75 g (yield 66%) of 2,2-bis(4-morpholinophenyl)propionic acid, having a melting point of 217°~223° C.

EXAMPLE 4

Synthesis of 2,2-bis(4-N-ethyl-N-ethoxyethylaminophenyl)propionic acid

Into 6 ml of 20% aqueous solution of sulfuric acid was dissolved 5.3 g of N-ethyl-N-ethoxyethylaniline. To the solution was added 3 g of pyruvic acid and the mixture was heated with reflux for 18 hours. The reaction mixture was, after cooled, diluted with 100 ml of water and adjusted to alkaline with addition of 20% aqueous solution of sodium hydroxide. Thereto was added 50 ml of benzene to remove by extraction unreacted N-ethyl-N-ethoxyethylaniline. The aqueous layer was adjusted to pH 6 with addition of 6N—HCl. A 2.7 g (yield 43%) of 2,2-bis(4-N-ethyl-N-ethoxyethylaminophenyl)propionic acid was obtained in the form of oil.

EXAMPLE 5

Synthesis of 2,2-bis(1-methyl-1,2,3,4-tetrahydroquinoline-6-yl)propionic acid Into 6.0 ml of 6N—HCl solution was dissolved 4.2 g of 1-methyl-1,2,3,4-tetrahydroquinoline. To the solution was added 3 g of pyruvic acid and the mixture was heated with reflux for 20 hours. The reaction mixture was, after cooled, diluted with 100 ml of water and adjusted to pH 6 with addition of 20% aqueous solution of sodium hydroxide. The precipitated crystal was collected by filtration which was 4.0 g (yield 77%) of 2,2-bis(1-methyl-1,2,3,4-tetrahydroquinoline-6-yl)propionic acid as light brown crystal, having a melting point of 155°~157° C.

EXAMPLES 6 to 29

Diphenylalkanoic acid derivatives as listed in Table 1 were prepared in the same manner as in Example 1 except that aniline derivatives and ketocarboxylic acid derivatives recited in Table 1 were used in place of N,N-dimethylaniline and pyruvic acid. Table 1 also shows a yield in each reaction.

TABLE 1

| Ex. | aniline derivative | ketocarboxylic acid derivative | Diphenylalkanoic acid derivative | Yield(%) |
|---|---|---|---|---|
| 6 | C₆H₅-N(C₂H₅)₂ | CH₃COCOOH | (C₂H₅)₂N-C₆H₄-C(CH₃)(COOH)-C₆H₄-N(C₂H₅)₂ | 72 |
| 7 | C₆H₅-N(C₆H₁₁)(CH₃) (H on N) | CH₃COCOOH | corresponding diphenyl product | 69 |
| 8 | (4-CH₃-C₆H₄)-N(C₆H₅)(C₂H₅) | CH₃COCOOH | corresponding diphenyl product | 68 |
| 9 | (4-Cl-C₆H₄-CH₂)-N(C₆H₅)(C₂H₅) | CH₃COCOOH | corresponding diphenyl product | 42 |
| 10 | (ClC₂H₄)-N(C₆H₅)(n-C₃H₇) | CH₃COCOOH | corresponding diphenyl product | 43 |
| 11 | (CH₂=CH-CH₂)-N(C₆H₅)(CH₃) | CH₃COCOOH | corresponding diphenyl product | 45 |

TABLE 1-continued

| Ex. | aniline derivative | ketocarboxylic acid derivative | Diphenylalkanoic acid derivative | Yield(%) |
|---|---|---|---|---|
| 12 | N-ethyl-N-((tetrahydropyran-2-yl)methyl)aniline | CH₃COCOOH | bis[4-(N-ethyl-N-((tetrahydropyran-2-yl)methyl)amino)phenyl]-substituted diphenylalkanoic acid | 38 |
| 13 | julolidine | CH₃COCOOH | bis-julolidinyl diphenylalkanoic acid | 81 |
| 14 | N-ethyl-N-(2-phenoxyethyl)aniline | CH₃COCOOH | bis[4-(N-ethyl-N-(2-phenoxyethyl)amino)phenyl] diphenylalkanoic acid | 63 |
| 15 | 2,5-dimethyl-1-phenylpyrrolidine | CH₃COCOOH | corresponding diphenylalkanoic acid | 65 |
| 16 | 2-phenyl-1,2,3,4-tetrahydroisoquinoline | CH₃COCOOH | corresponding diphenylalkanoic acid | 45 |
| 17 | 1-phenylhexamethyleneimine | CH₃COCOOH | corresponding diphenylalkanoic acid | 52 |

TABLE 1-continued
| Ex. | aniline derivative | ketocarboxylic acid derivative | Diphenylalkanoic acid derivative | Yield(%) |
|---|---|---|---|---|
| 18 | 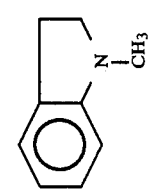 | CH₃COCOOH | 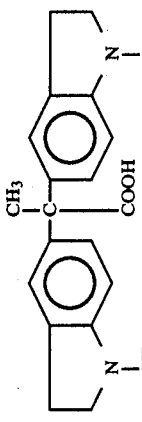 | 67 |
| 19 | 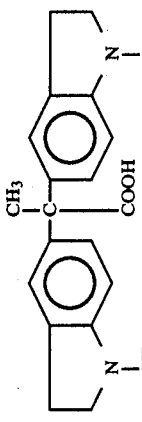 | CH₃COCOOH | 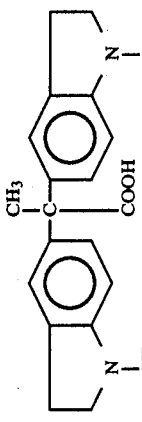 | 78 |
| 20 | 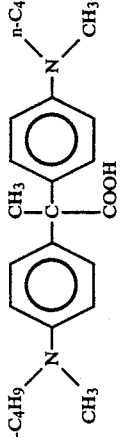 | CH₃COCOOH | 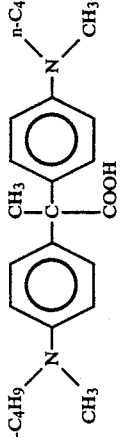 | 55 |
| 21 | 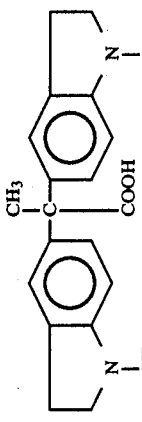 | C₂H₅COCOOH | 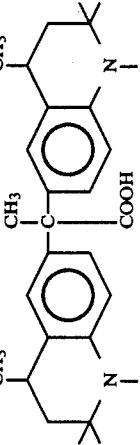 | 66 |
| 22 | 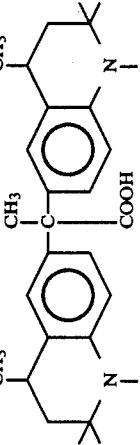 | n-C₄H₉COCOOH | 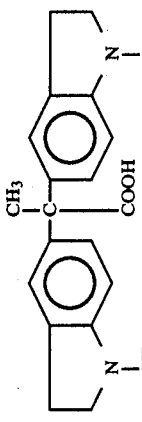 | 48 |
| 23 | 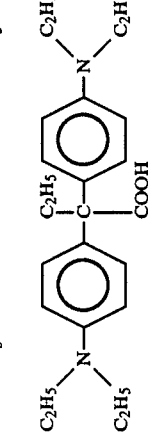 | 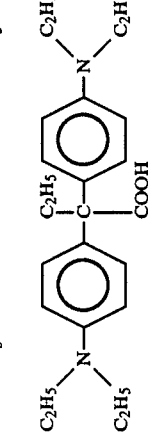 | 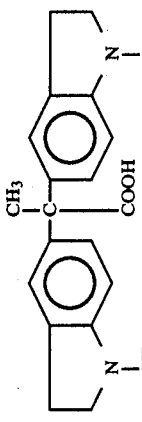 | 63 |

TABLE 1-continued

| Ex. | aniline derivative | ketocarboxylic acid derivative | Diphenylalkanoic acid derivative | Yield(%) |
|---|---|---|---|---|
| 24 | C₆H₅-N(pyrrolidine) | CH₃COCOOCH₂-C₆H₅ | bis(4-pyrrolidinylphenyl)-C(CH₃)(COOCH₂C₆H₅) | 58 |
| 25 | C₆H₅-N(pyrrolidine) | CH₃COCONH-C₆H₄-CH₃ | bis(4-pyrrolidinylphenyl)-C(CH₃)(CONH-C₆H₄-CH₃) | 60 |
| 26 | C₆H₅-N(pyrrolidine) | CH₃COCON(n-C₄H₉)₂ | bis(4-pyrrolidinylphenyl)-C(CH₃)(CON(n-C₄H₉)₂) | 73 |
| 27 | C₆H₅-N(pyrrolidine) | C₂H₅COCOOC₂H₅ | bis(4-pyrrolidinylphenyl)-C(C₂H₅)(COOC₂H₅) | 70 |
| 28 | C₆H₅-N(pyrrolidine) | CH₃COCOOC₂H₅ | bis(4-pyrrolidinylphenyl)-C(CH₃)(COOC₂H₅) | 79 |
| 29 | C₆H₅-N(iso-C₃H₇)(CH₃) | CH₃COCOOH | bis(4-(N-iso-C₃H₇-N-CH₃)aminophenyl)-C(CH₃)(COOH) | 43 |

EXAMPLE 30

Synthesis of 1,1-bis(4-dimethylaminophenyl)ethylene

Into 400 ml of benzene was dissolved 10 g of 2,2-bis(4-dimethylaminophenyl)propionic acid. Thereto was added 10 g of lead dioxide and the mixture was reacted at room temperature with stirring for 30 minutes. The lead compound was removed by filtration and the benzene layer was washed with 200 ml of 5% aqueous solution of sodium hydroxide. Benzene was removed by distillation at a reduced pressure. The residue was recrystallized from methanol to obtain 6.3 g (yield 74%) of 1,1-bis(4-dimethylaminophenyl)ethylene, having a melting point of 123°~123.5° C.

EXAMPLE 31

Synthesis of 1,1-bis(4-pyrrolidinophenyl)ethylene

Into 500 ml of toluene was dissolved 5 g of 2,2-bis(4-pyrrolidinophenyl)propionic acid. Thereto was added 3.7 g of lead dioxide and the mixture was reacted at room temperature with stirring for one hour. The lead compound was removed by filtration and the toluene layer was washed with 100 ml of 5% aqueous solution of sodium hydroxide. Toluene was removed by distillation at a reduced pressure. The residue was recrystallized from ethanol to obtain 3.3 g (yield 76%) of 1,1-bis(4-pyrrolidinophenyl)ethylene, having a melting point of 220°~223° C.

EXAMPLE 32

Synthesis of 1,1-bis(4-morpholinophenyl)ethylene

Into 200 ml of toluene was dissolved 10 g of 2,2-bis(4-morpholinophenyl)propionic acid. Thereto was added 7.2 g of lead dioxide and the mixture was reacted at reflux temperature with stirring for one hour. The lead compound was removed by filtration and the toluene layer was extracted with 200 ml of 3% aqueous solution of sodium hydroxide to recover the unreacted starting material. The remained toluene solution was concentrated at a reduced pressure to obtain crystals. The crystal was recrystallized from n-propanol to obtain 4.1 g (yield 46.3%) of 1,1-bis(4-morpholinophenyl)ethylene, having a melting point of 203°~205° C. The starting 2,2-bis(4-morpholinophenyl)propionic acid was recovered in an amount of 3.8 g.

EXAMPLE 33

Synthesis of 1,1-bis(4-N-propargyl-N-ethylaminophenyl)ethylene

Into 300 ml of benzene was dissolved 10 g of 2,2-bis(4-N-propargyl-N-ethylaminophenyl)propionic acid. Thereto were added 1 ml of pyridine and 11.5 g of lead tetraacetate and the mixture was reacted at 70° C. for 3 hours. After completion of the reaction, the insolubles were removed by filtration and the benzene layer was washed with 100 ml of water and 100 ml of 5% aqueous solution of sodium hydroxide. The layer was concentrated at a reduced pressure to give 6.3 g (yield 71.5%) of 1,1-bis(4-N-propargyl-N-ethylaminophenyl)ethylene in the form of a viscous liquid.

EXAMPLE 34

Synthesis of 1-phenyl-1-(4-pyrrolidinophenyl)ethylene

The reaction was conducted in the same manner as in Example 32 except that 10 g of 2-phenyl-2-(4-pyrrolidinophenyl)propionic acid was used in place of 2,2-bis(4-morpholinophenyl)propionic acid to obtain 5.9 g (yield 69.9%) of 1-phenyl-1-(4-pyrrolidinophenyl)ethylene, having a melting point of 82.5°~83.0° C.

EXAMPLE 35

Synthesis of 1-(4-methoxyphenyl)-1-(4-dimethylaminophenyl)ethylene

The reaction was conducted in the same manner as in Example 32 except that 10 g of 2-(4-methoxyphenyl)-2-(4-dimethylaminophenyl)propionic acid was used in place of 2,2-bis(4-morpholinophenyl)propionic acid to obtain 6.4 g (yield 75.6%) of 1-(4-methoxyphenyl)-1-(4-dimethylaminophenyl)ethylene, having a melting point of 124°~126° C.

EXAMPLE 36

Synthesis of 1,1-bis(4-dimethylaminophenyl)-1-propene

The reaction was conducted in the same manner as in Example 30 except that 10 g of 2,2-bis(4-dimethylaminophenyl)butyric acid was used in place of 2,2-bis(4-dimethylaminophenyl)propionic acid to obtain 6.6 g (yield 76.8%) of 1,1-bis(4-dimethylaminophenyl)-1-propene, having a melting point of 99°~101° C.

EXAMPLE 37

Synthesis of 1-(4-methoxyphenyl)-1-(4-pyrrolidinophenyl)ethylene

Into 50 ml of 5% aqueous solution of sodium hydroxide was dissolved 5 g of 2-(4-methoxyphenyl)-2-(4-pyrrolidinophenyl)propionic acid. Thereto was gradually added dropwise 2.4 g of 35% aqeous solution of hydrogen peroxide and the mixture was reacted at room temperature with stirring for 2 hours, and further at 60° C. with stirring for one hour. The reaction mixture was cooled and the precipitated crystal was collected by filtration. The crystal was recrystallized from methanol to give 3.0 g (yield 69.9%) of 1-(4-methoxyphenyl)-1-(4-pyrrolidinophenyl)ethylene, having a melting point of 159°~162° C.

EXAMPLE 38

Synthesis of 1,1-bis(4-diethylaminophenyl)ethylene

Into 200 ml of 1N—HCl solution was dissolved 10 g of 2,2-bis(4-diethylaminophenyl)propionic acid. Thereto was gradually added 5.7 g of ferric chloride at room temperature and the mixture was reacted with stirring for 2 hours. The reaction mixture was adjusted to alkaline with addition of aqueous solution of sodium hydroxide and then extracted with 50 ml of toluene. The toluene layer was concentrated at a reduced pressure to obtain crystals. The crystal was recrystallized from ethanol to give 6.5 g (yield 74.3%) of 1,1-bis(4-diethylaminophenyl)ethylene, having a melting point of 100°~102° C.

EXAMPLE 39

Synthesis of 1,1-bis(4-pyrrolidinophenyl)ethylene

Into 100 ml of 5% aqueous solution of sodium hydroxide was dissolved 10 g of 2,2-bis(4-pyrrolidinophenyl)propionic acid. Thereto was added 9.2 g of potassium persulfate and the mixture was reacted with stirring for one hour. The resulting precipitates were collected by filtration and recrystallized from methanol to obtain 7.0 g (yield 80%) of 1,1-bis(4-pyrrolidinophenyl)ethylene, having a melting point of 221°~223° C.

EXAMPLE 40

Synthesis of 1-(4-methylphenyl)-1-(4-pyrrolidinophenyl)ethylene

The reaction was conducted in the same manner as in Example 39 except that 2-(4-methylphenyl)-2-(4-pyrrolidinophenyl)propionic acid was used in place of 2,2-bis(4-pyrrolidinophenyl)propionic acid. The precipitates were recrystallized from ethanol to obtain 6.0 g (yield 70.5%) of 1-(4-methylphenyl)-1-(4-pyrrolidinophenyl)ethylene, having a melting point of 134°~136° C.

EXAMPLE 41

Synthesis of 1-(4-dimethylaminophenyl)-1-(2-methyl-4-dimethylaminophenyl)ethylene The reaction was conducted in the same manner as in Example 38 except that 2-(4-dimethylaminophenyl)-2-(2-methyl-4-dimethylaminophenyl)propionic acid was used in place of 2,2-bis(4-diethylaminophenyl)propionic acid. The precipitates were recrystallized from methanol to obtain 6.3 g (yield 73.3%) of 1-(4-dimethylaminophenyl)-1-(2-methyl-4-dimethylaminophenyl)ethylene, having a melting point of 90°~91° C.

EXAMPLE 42

Synthesis of 1-phenyl-1-(4-dimethylaminophenyl)ethylene

The reaction was conducted in the same manner as in Example 37 except that 2-phenyl-2-(4-dimethylaminophenyl)propionic acid was used in place of 2,2-bis(4-dimethylaminophenyl)propionic acid. The precipitates were recrystallized from ethanol to obtain 2.9 g (yield 70.0%) of 1-phenyl-1-(4-dimethylaminophenyl)ethylene, having a melting point of 51°~52° C.

EXAMPLE 43

Synthesis of 1-(4-dimethylaminophenyl)-1-(4-pyrrolidinophenyl)ethylene

The reaction was conducted in the same manner as in Example 39 except that 2-(4-dimethylaminophenyl)-2-(4-pyrrolidinophenyl)propionic acid was used in place of 2,2-bis(4-pyrrolidinophenyl)propionic acid. The precipitates were recrystallized from ethanol to obtain 6.7 g (yield 77.6%) of 1-(4-dimethylaminophenyl)-1-(4-pyrrolidinophenyl)ethylene, having a melting point of 149°~150° C.

EXAMPLE 44

Synthesis of 1-(4-dimethylaminophenyl)-1-(2-methyl-4-pyrrolidinophenyl)ethylene The reaction was conducted in the same manner as in Example 39 except that 2-(4-dimethylaminophenyl)-2-(2-methyl-4-pyrrolidinophenyl)propionic acid was used in place of 2,2-bis(4-pyrrolidinophenyl)propionic acid. The precipitates were recrystallized from ethanol to obtain 6.6 g (yield 75.9%) of 1-(4-dimethylaminophenyl)-1-(2-methyl-4-pyrrolidinophenyl)ethylene, having a melting point of 90°~93° C.

EXAMPLES 45 TO 68

Diphenylalkene derivatives as listed in Table 2 were prepared in accordance with Example as recited in Table 2 with use of the listed diphenylalkanoic acid derivatives. Table 2 also shows a yield in each reaction.

TABLE 2

| Ex. | Diphenylalkanoic acid derivative | Diphenylalkene derivative | Ex. No. | Yield (%) |
|---|---|---|---|---|
| 45 | 2,2-bis(4-N—methyl-N—ethylaminophenyl)propionic acid | 1,1-bis(4-N—methyl-N—ethylaminophenyl)ethylene | 33 | 72 |
| 46 | 2,2-bis{4-di(p-chlorobenzyl)aminophenyl}propionic acid | 1,1-bis{4-di(p-chlorobenzyl)aminophenyl}ethylene | 31 | 66 |
| 47 | 2,2-bis(4-N—ethyl-N—allylaminophenyl)propionic acid | 1,1-bis(4-N—ethyl-N—allylaminophenyl)ethylene | 38 | 71 |
| 48 | 2,2-bis(1-ethyl-1,2,3,4-tetrahydroquinoline-6-yl)propionic acid | 1,1-bis(1-ethyl-1,2,3,4-tetrahydroquinoline-6-yl)ethylene | 30 | 77 |
| 49 | 2,2-bis(4-N—methyl-N—n-butylaminophenyl)propionic acid | 1,1-bis(4-N—methyl-N—n-butylaminophenyl)ethylene | 31 | 72 |
| 50 | 2,2-bis(4-hexamethyleneiminophenyl)propionic acid | 1,1-bis(4-hexamethyleneiminophenyl)ethtylene | 39 | 74 |
| 51 | 2,2-bis(julolidine-9-yl)propionic acid | 1,1-bis(julolidine-9-yl)ethylene | 39 | 66 |
| 52 | 2,2-bis(4-N—methyl-N—cyclohexylaminophenyl)propionic acid | 1,1-bis(4-N—methyl-N—cyclohexylaminophenyl)ethylene | 30 | 69 |
| 53 | 2,2-bis(4-N—ethyl-N—β-chloroethylaminophenyl)propionic acid | 1,1-bis(4-N—ethyl-N—β-chloroethylaminophenyl)ethylene | 37 | 70 |
| 54 | 2,2-bis(4-N—ethyl-N—benzylaminophenyl)propionic acid | 1,1-bis(4-N—ethyl-N—benzylaminophenyl)ethylene | 32 | 63 |
| 55 | 2,2-bis(4-N—methyl-N—p-tolylaminophenyl)propionic acid | 1,1-bis(4-N—methyl-N—p-totylaminophenyl)ethylene | 32 | 71 |

TABLE 2-continued

| Ex. | Diphenylalkanoic acid derivative | Diphenylalkene derivative | Ex. No. | Yield (%) |
|---|---|---|---|---|
| 56 | 2,2-bis(4-N—methyl-N—β-methoxyethyl-aminophenyl)propionic acid | 1,1-bis(4-N—methyl-N—β-methoxyethylamino-phenyl)ethylene | 39 | 78 |
| 57 | 2-(4-ethoxyphenyl)-2-(4-pyrrolidino-phenyl)propionic acid | 1-(4-ethoxyphenyl)-1-(4-pyrrolidino-phenyl)ethylene | 32 | 64 |
| 58 | 2-(4-ethylphenyl)-2-(4-pyrrolidinophenyl)-propionic acid | 1-(4-ethylphenyl)-1-(4-pyrrolidino-phenyl)ethylene | 37 | 72 |
| 59 | 2-(4-diethylamino-phenyl)-2-(4-dimethylamino-2-methylphenyl)propionic acid | 1-(4-diethylamino-phenyl-1-(4-dimethylamino-2-methylphenyl)ethylene | 37 | 74 |
| 60 | 2-phenyl-2-(4-N—ethyl-N—allylamino-phenyl)propionic acid | 1-phenyl-1-(4-N—ethyl-N—allyl-aminophenyl)ethylene | 31 | 69 |
| 61 | 2-(2,4-dimethoxy-phenyl)-2-(4-diethyl-aminophenyl)propionic acid | 1-(2,4-dimethoxy-phenyl-1-(4-diethylaminophenyl)-ethylene | 38 | 68 |
| 62 | 2-(4-methylphenyl)-2-(4-di-n-butylamino-phenyl)propionic acid | 1-(4-methylphenyl)-1-(4-di-n-butyl-aminophenyl)ethylene | 38 | 67 |
| 63 | 2-(4-diethylamino-phenyl)-2-(4-pyrrolidinophenyl)-propionic acid | 1-(4-diethylamino-phenyl)-1-(4-pyrrolidinophenyl)-ethylene | 32 | 77 |
| 64 | 2-(4-chlorophenyl)-2-(4-pyrrolidino-phenyl)propionic acid | 1-(4-chlorophenyl)-1-(4-pyrrolidino-phenyl)ethylene | 37 | 76 |
| 65 | 2,2-bis(4-pyrrolidinophenyl)-butyric acid | 1,1-bis(4-pyrrolidinophenyl)-1-propene | 30 | 82 |
| 66 | 2-(4-methoxyphenyl)-2-(4-pyrrolidino-phenyl)butyric acid | 1-(4-methoxyphenyl)-1-(4-pyrrolidino-phenyl)-1-propene | 39 | 78 |
| 67 | 2-(4-methoxyphenyl)-2-(1-ethyl-1,2,3,4-tetrahydroquinoline-6-yl)propionic acid | 1-(4-methoxyphenyl)-1-(1-ethyl-1,2,3,4-tetrahydroquinoline-6-yl)ethylene | 39 | 78 |
| 68 | 2-(4-methoxyphenyl)-2-(1-ethyl-1,2,3,4-tetrahydroquinoline-6-yl)butyric acid | 1-(4-methoxyphenyl)-1-(1-ethyl-1,2,3,4-tetrahydroquinoline-6-yl)-1-propene | 39 | 80 |

As apparent from examples, the present invention provides a process for preparing diphenylalkanoic acid derivatives and diphenylalkene derivatives with relatively mild reaction conditions without use of a specific reaction apparatus and with extremely simple purification and isolation operations. Further, in the present invention, asymmetrical diphenylalkene derivatives are also easily prepared.

We claim:

1. A process for preparing a diphenylalkene derivative of formula (II)

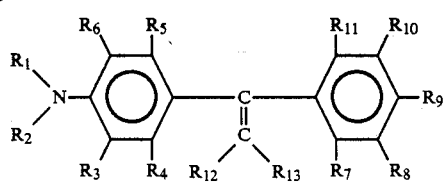

(II)

which comprises oxidizing a diphenylalkanoic acid derivative of formula (I)

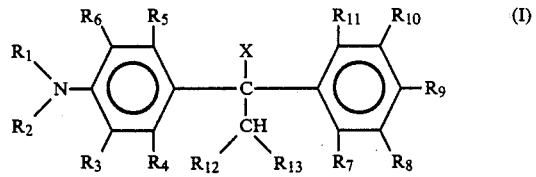

(I)

wherein
each of $R_1$ and $R_2$ is selected independently from the group consisting of $C_{1-8}$ alkyl; $C_{2-4}$ alkyl substituted with $C_{1-4}$ alkoxyl; $C_{2-4}$ alkyl substituted with halogen atom; $C_{3-9}$ alkenyl; $C_{3-9}$ alkynyl; $C_{5-12}$ cycloalkyl; phenyl-$C_{1-4}$ alkyl unsubstituted or substituted with halogen atom, $C_{1-4}$ alkyl or $C_{1-4}$ alkoxyl; phenyl unsubstituted or substituted with halogen atom, $C_{1-4}$ alkyl or $C_{1-4}$ alkoxyl; or $R_1$ and $R_2$ form together with the nitrogen atom to which $R_1$ and $R_2$ are attached, or together with said nitrogen atom and the phenyl ring to which said nitrogen atom is attached, a heteroring selected from the group consisting of pyrrolidine, piperidine, morpholine, hexamethyleneimine, isoindoline, tetrahydroquinoline, indoline and julolidine, each of $R_3$ to $R_{11}$ is independently selected from the group consisting of hydrogen atom; halogen atom; $C_{1-4}$ alkyl; $C_{1-4}$ alkoxyl; phenoxy unsubstituted or substituted with halogen atom, $C_{1-4}$ alkyl or $C_{1-4}$ alkoxyl; and the amino group —$N(R_{17})(R_{18})$ wherein each of $R_{17}$ and $R_{18}$ is independently selected from the group consisting of hydrogen atom; $C_{1-8}$ alkyl; $C_{2-4}$ alkyl substituted with $C_{1-4}$ alkoxyl; $C_{2-4}$ alkyl substituted with halogen atom; $C_{3-9}$ alkenyl; $C_{3-9}$ alkynyl; $C_{5-12}$ cycloalkyl; $C_{1-4}$ acyl; phenyl-$C_{1-4}$ alkyl unsubstituted or substituted with halogen atom, $C_{1-4}$ alkyl or $C_{1-4}$ alkoxyl; and phenyl unsubstituted or substituted with halogen atom, $C_{1-4}$ alkyl or $C_{1-4}$ alkoxyl, provided that $R_{17}$ and $R_{18}$ are not hydrogen atoms simultaneously, and $R_{17}$ and $R_{18}$ may form together with the nitrogen atom to which $R_{17}$ and $R_{18}$ are attached, or together with said nitrogen atom and the phenyl ring to which said nitrogen atom is attached, a heteroring selected from the group consisting of pyrrolidine, piperidine, morpholine, hexamethyleneimine, isoindoline, tetrahydroquinoline, indoline and julolidine, each of $R_{12}$ and $R_{13}$ is independently hydrogen atom or $C_{1-4}$ alkyl, X is carboxyl, or an amide, ester or halide thereof, said oxidation being conducted at a temperature in the range of from −5° C. to 150° C., in a solvent which is at least one member selected from the group consisting of water and an inert organic solvent, and in the presence of an oxidizing agent selected from the group consisting of lead dioxide, lead tetraacetate, ferric chloride, potassium persulfate, sodium persulfate, ammonium persulfate and hydrogen peroxide.

2. A process as defined in claim 1 wherein the diphenylalkanoic acid derivative is a compound of the formula [III]

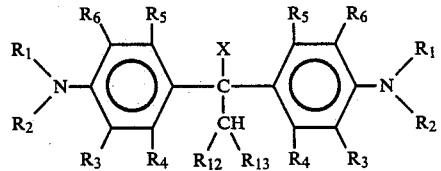

wherein $R_1$ to $R_6$, $R_{12}$, $R_{13}$ and X are same as in claim 1.

3. A process as defined in claim 1, wherein the diphenylalkanoic acid derivative is a compound of formula (IV).

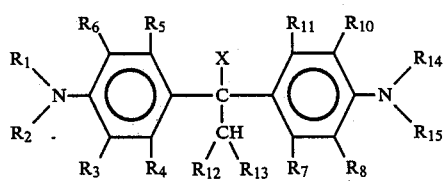

wherein
each of $R_{14}$ and $R_{15}$ is independently selected from the group consisting of $C_{1-8}$ alkyl; $C_{2-4}$ alkyl substituted with $C_{1-4}$ alkoxyl; $C_{2-4}$ alkyl substituted with halogen atom; $C_{3-9}$ alkenyl; $C_{3-9}$ alkynyl; $C_{5-12}$ cycloalkyl; phenyl-$C_{1-4}$ alkyl unsubstituted or substituted with halogen atom, $C_{1-4}$ alkyl or $C_{1-4}$ alkoxyl; and phenyl unsubstituted or substituted with halogen atom, $C_{1-4}$ alkyl or $C_{1-4}$ alkoxyl; or $R_{14}$ and $R_{15}$ form together with the nitrogen atom to which $R_{14}$ and $R_{15}$ are attached, or together with said nitrogen atom and the phenyl ring to which said nitrogen atom is attached, a heteroring selected from the group consisting of pyrrolidine, piperidine, morpholine, hexamethyleneimine, isoindoline, tetrahydroquinoline, indoline and julolidine, with the proviso that $R_1$ and $R_{14}$ are not the same group, and each of $R_1$ to $R_8$, $R_{10}$ to $R_{13}$ and X is as defined in claim 1.

4. A process as defined in claim 1 wherein the diphenylalkanoic acid derivative is a compound of the formula [V]

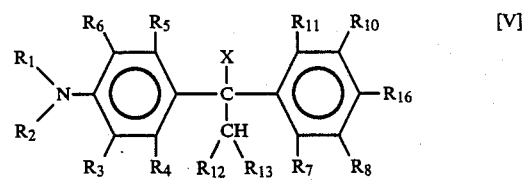

wherein $R_{16}$ is selected from the group consisting of hydrogen atom, halogen atom, $C_{1-4}$ alkyl, $C_{1-4}$ alkoxyl, and phenoxy unsubstituted or substituted with a substituent selected from the group consisting of halogen atom, $C_{1-4}$ alkyl and $C_{1-4}$ alkoxyl, $R_1$ to $R_8$, to $R_{10}$ to $R_{13}$ and X are same as in claim 1.

5. A process as defined in claim 2 wherein the diphenylalkanoic acid derivative is a compound of the formula [III']

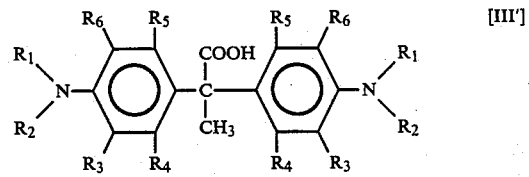

wherein $R_1$ to $R_6$ are same as in claim 2.

6. A process as defined in claim 3 wherein the diphenylalkanoic acid derivative is a compound of the formula [IV']

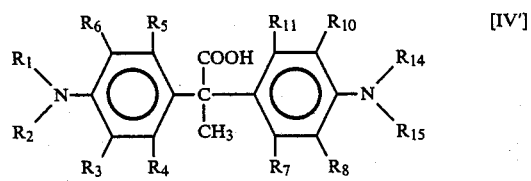

wherein $R_1$ to $R_8$, $R_{10}$, $R_{11}$, $R_{14}$ and $R_{15}$ are same as in claim 3.

7. A process as defined in claim 4 wherein the diphenylalkanoic acid derivative is a compound of the formula [V']

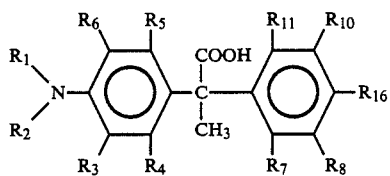

wherein $R_1$ to $R_8$, $R_{10}$, $R_{11}$ and $R_{16}$ are same as in claim 4.

8. A process as defined in claim 5 wherein the diphenylalkanoic acid derivative is a compound of the formula [III'']

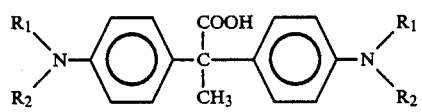

wherein $R_1$ and $R_2$ are same as in claim 5.

9. A process as defined in claim 6 wherein the diphenylalkanoic acid derivative is a compound of the formula [IV'']

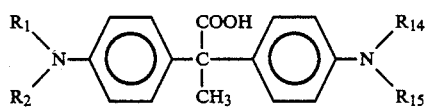

wherein $R_1$, $R_2$, $R_{14}$ and $R_{15}$ are same as in claim 6.

10. A process as defined in claim 7 wherein the diphenylalkanoic acid derivative is a compound of the formula [V'']

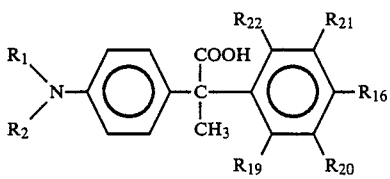

wherein $R_1$, $R_2$ and $R_{16}$ are same as in claim 7, $R_{19}$ to $R_{22}$ are each same as $R_{16}$.

11. A process as defined in claim 2, wherein the diphenylalkanoic acid derivative is a compound of formula (III) which is obtained by reacting an aniline derivative of formula (VI) with a ketocarboxylic acid derivative of formula (VII)

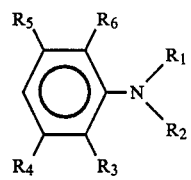

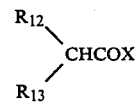

wherein each of $R_1$ to $R_6$, $R_{12}$ and $R_{13}$ is as defined in claim 2.

* * * * *